(12) United States Patent
Yuan et al.

(10) Patent No.: US 11,716,944 B1
(45) Date of Patent: Aug. 8, 2023

(54) METHOD FOR IMPROVING ONE-TIME SEEDLING RATE OF MICROSPORE EMBRYOIDS OF BRASSICA CAMPESTRIS SSP. CHINENSIS MAKINO

(71) Applicants: Anhui Agricultural University, Hefei (CN); Anhui Wanjiang Vegetable Industry Technology Research Institute Co., Ltd., Ma'anshan City (CN)

(72) Inventors: Lingyun Yuan, Hefei (CN); Liting Zhang, Hefei (CN); Chenggang Wang, Hefei (CN); Xingxue Huang, Hefei (CN); Shidong Zhu, Hefei (CN); Jinlong Zhang, Hefei (CN); Jinfeng Hou, Hefei (CN); Xiaoyan Tang, Hefei (CN); Zegen Zhang, Hefei (CN)

(73) Assignees: Anhui Agricultural University, Hefei (CN); Anhui Wanjiang Vegetable Industry Technology Research Institute Co., Ltd., Ma'anshan (CN)

( * ) Notice: Subject to any disclaimer, the term of this patent is extended or adjusted under 35 U.S.C. 154(b) by 0 days.

(21) Appl. No.: 17/948,948

(22) Filed: Sep. 20, 2022

(30) Foreign Application Priority Data

Sep. 26, 2021 (CN) .......................... 202111130761.5

(51) Int. Cl.
*A01H 4/00* (2006.01)
*C12N 5/04* (2006.01)

(52) U.S. Cl.
CPC .................. *A01H 4/005* (2013.01); *C12N 5/04* (2013.01)

(58) Field of Classification Search
CPC ...................................... A01H 4/005
See application file for complete search history.

(56) References Cited

U.S. PATENT DOCUMENTS 5,900,375 A 5/1999 Simmonds et al.

FOREIGN PATENT DOCUMENTS

| CN | 102388800 | A |   | 3/2012 |
|----|-----------|---|---|--------|
| CN | 102144560 | B | * | 9/2013 |
| CN | 104818296 | A | * | 8/2015 |
| CN | 110089426 | A |   | 8/2019 |
| CN | 110731271 | A | * | 1/2020 |
| CN | 112385541 | A |   | 2/2021 |

* cited by examiner

*Primary Examiner* — Charles Logsdon
*Assistant Examiner* — Wayne Zhong

(57) ABSTRACT

The present invention provides a method for improving a one-time seedling rate of microspore embryoids of *Brassica campestris ssp. Chinensis Makino*, including the steps of: spraying 6-BA onto a flower bud of a plant; sterilizing the flower bud with alcohol and $HgCl_2$; releasing microspores, filtering and centrifuging to obtain purified microspores; diluting the microspores with a NLN medium, subpackaging into culture dishes, and adding phytic acid; finally, subjecting to heat shock treatment and transferring to culture in the dark until embryoids appear, and then conducting shaking culture; transferring the cultured embryos in a cotyledon stage onto a MS medium for differentiation culture, wherein the culture conditions are: 4° C., 14 h of illumination by blue-red compound light/day, and 14 days of culture; and then continuing to culture under the condition of 25° C. and 14 h of illumination by blue-red compound light/day until seedlings.

7 Claims, No Drawings

METHOD FOR IMPROVING ONE-TIME SEEDLING RATE OF MICROSPORE EMBRYOIDS OF BRASSICA CAMPESTRIS SSP. CHINENSIS MAKINO

CROSS-REFERENCE TO RELATED APPLICATIONS

This Application claims priorities from the Chinese patent application 202111130761.5 filed Sep. 26, 2021, the content of which are incorporated herein in the entirety by reference.

FIELD OF TECHNOLOGY

The present invention relates to the field of biotechnology, and in particular to a method for improving a one-time seedling rate of microspore embryoids of *Brassica campestris ssp. Chinensis Makino*.

BACKGROUND

*Brassica campestris ssp. Chinensis Makino* belongs to a cabbage subspecies of the species of *brassica campestris* in *Brassica* of Cruciferae, and is commonly known as Chinese cabbage, pakchoi and rape. *Brassica campestris ssp. Chinensis Makino* originates in China and has a long history of cultivation. It is a popular main vegetable that people in the south like to eat all the year round.

Spores are a kind of cells produced by a plant, which has the function of reproduction or dormancy and can directly develop into a new individual. Microspores are monocytes released by a tetrad after meiosis of a male gametophyte of a higher plant. Culture of isolated microspores refers to a method of obtaining a microspore population directly from a flower bud or an anther for culture. Since microspore culture is more efficient than anther culture and it can also eliminate the influence of somatic cells such as an anther wall and a tapetum tissue, it is favored by breeders.

Theoretically, after being cultured in a liquid medium for a period of time, the microspores will go through embryoids in different periods, and finally form cotyledon embryoids. At this time, they can be transferred onto a solid regeneration medium to culture regenerated plantlets. However, in fact, the embryoids transferred onto the solid regeneration medium may not necessarily develop into normal regenerated plantlets. The main reasons are of the following several aspects: (1) most microspore-derived embryos may develop abnormally, including the formation of secondary embryos on hypocotyls; and (2) the plant regeneration frequency of embryoids transferred onto the solid medium is also affected by many factors, such as medium composition, moisture, light quality, etc.; and when the culture conditions are not appropriate, the plant regeneration is difficult and the seedling rate is low. Therefore, if we can avoid the problem of "abnormal embryo development" in the process of microspore culture, and meanwhile find the best cultivation conditions in the process of plant regeneration, the regeneration frequency of the embryoids can be effectively increased and the one-time seedling rate of the embryoids is improved.

SUMMARY

The technical problem to be solved by the present invention is to provide a method for improving a one-time seedling rate of microspore embryoids of *Brassica campestris ssp. Chinensis Makino*; which avoids the problem of abnormal embryoid development by "adjusting the temperature during embryoid regeneration", and avoids the problems of difficult plant regeneration and low seedling rate when the culture conditions are not appropriate by "externally spraying 6-BA onto a flower bud", "adding phytic acid into the medium in a process of microspore culture" and "adjusting the spectral conditions during embryoid regeneration".

The present invention adopts the following technical solutions to solve the aforementioned technical problems:

A method for improving a one-time seedling rate of microspore embryoids of *Brassica campestris ssp. Chinensis Makino* includes the steps of:

(1) pretreatment of flower bud spraying a concentration of 50-150 mg/L of 6-BA onto a flower bud of a plant of *Brassica campestris ssp. Chinensis Makino* after squaring; and taking an inflorescence for later use on the next day after the spraying of 6-BA;

(2) isolation of microspores selecting a flower bud with a petal length/anther length between 0.5-1, conducting combined sterilization with 70% alcohol and 0.1% $HgCl_2$, and then rinsing with sterilized water; then, crushing the bud in a B5 medium to release microspores, and filtering the microspores by a steel-wire mesh screen and a cell mesh screen successively; subsequently, collecting a filtrate into a centrifugal tube for centrifuging; and after the centrifuging, resuspending a pellet with a B5 medium and centrifuging again to obtain a pellet as desired purified microspores;

(3) culture of microspores diluting the purified microspores with a NLN medium, and adjusting a cell density to $1 \times 10^5 - 2 \times 10^5$ /mL$^{-1}$; subsequently, subpackaging the diluted purified microspores into culture dishes, and adding phytic acid PA at a concentration of 0.01%-0.5%; and finally, subjecting to heat shock treatment at 33° C. for 24 h, then transferring to culture in the dark at 25° C., and placing onto a shaker for shaking culture after embryoids visible to naked eyes appear; and (4) germination and seedling of embryoids transferring the cultured embryoids in a cotyledon stage onto a MS medium for differentiation culture, wherein culture conditions are: 4° C., 14 h of illumination by blue-red compound light/day, and 14 days of culture; and then, continuing to culture under a condition of 25° C. and 14 h of illumination by blue-red compound light/day until seedling.

As one of the preferred embodiments of the present invention, in the step (1), the selected inflorescence is specifically a main inflorescence or a healthy inflorescence of a primary branch of a plant without insect pests and cracked buds.

As one of the preferred embodiments of the present invention, in the step (1), after selected, the corresponding inflorescence is placed in a self-sealing bag and sprayed with clean water, and then stored in a refrigerator at 4° C. for 1-2 days for later use.

As one of the preferred embodiments of the present invention, in the step (2), a specific method of combined sterilization of the flower bud is: firstly sterilizing with 70% alcohol for 30 s, and then sterilizing with 0.1% $HgCl_2$ under shaking for 6 min; and after the combined sterilization is completed, the flower bud is rinsed with sterilized water for 2-3 times, with each time for 5 min.

As one of the preferred embodiments of the present invention, in the step (2), after the sterilization and cleaning of the selected bud is completed, the bud is crushed in the B5 medium with a glass rod to release the microspores, and then filtered by a 300 mesh steel-wire mesh screen and a cell mesh screen successively; subsequently, the filtrate is collected in a centrifuge tube and centrifuged under a condition of 1,000 r/min for 3 min; and after the centrifugation, the pellet is resuspended with the B5 medium and the resuspended solution is centrifuged again at 1,000 r/min for 3 min, and the finally obtained pellet is the purified microspores desired for the objective.

As one of the preferred embodiments of the present invention, in the step (3), the culture medium is pale yellow when the cell density of the microspores is $1 \times 10^5 - 2 \times 10^5$ /mL$^{-1}$.

As one of the preferred embodiments of the present invention, in the step (4), a length of the embryoids in a cotyledon stage transferred onto the MS medium is 2.5-3 mm.

As one of the preferred embodiments of the present invention, in the step (4), the ratio of blue light to red light in the blue-red compound light is 1:1.

As one of the preferred embodiments of the present invention, the B5 medium, the NLN medium and the MS medium are conventional media in the art, and their formulas are not described here any more.

The design idea and principle of the present invention:

I. On the problem of "possible abnormal development of embryos derived from microspores":

It has been proved by experiments that the older embryoids or embryoids cultured at higher temperature (25° C.) are more likely to have secondary embryogenesis, while the embryoids cultured at lower temperature are more likely to develop into normal plants. Therefore, during seedlings by embryoids regeneration, the abnormal development of the embryoids can be avoided by low-temperature pretreatment, thereby increasing the regeneration frequency of the embryoids and improving the seedling rate.

II. On the problem that "the plant regeneration frequency of the embryoids transferred onto the solid medium is also affected by many factors":

6-BA is a high-efficiency plant growth regulator, which performs well in many aspects such as promoting germination, promoting flower bud differentiation and flowering, increasing fruit setting rate, promoting fruit growth and improving fruit quality. It has been proved by experiments that externally spraying an appropriate concentration of 6-BA onto the flower bud can effectively improve the vitality of the microspores, which is thus conducive to the subsequent regeneration culture of the plants.

Phytic acid ($C_6H_{18}O_{24}P_6$) is a natural antioxidant. It has been found by research that, adding proper amount of phytic acid into the solid and liquid media can significantly reduce the activity of polyphenol oxidase, stabilize a pH value and a mV value in the media, promote the growth of plant cells, and enhance the ability of cells to resist browning and water-soaking, thereby improving the state of the cells.

The effect of light quality on plant growth is mainly embodied in the aspect of morphogenesis. Red light promotes the elongation of stems and petioles of a plant, while blue light affects an endogenous hormone of a plant, and enables free IAA and GA1 to decrease and enables ABA and ethylene content to increase. It has been proved by experiments that, after the microspores are subjected to appropriate treatment with the blue-red compound light at the early stage of germination of the microspores, the photoautotrophy ability of the microspores is greatly improved, the plants are robust, the morphogenesis is the best, and the seedling rate is high.

Therefore, in the process of regeneration culture of the embryoids, the regeneration frequency of the embryoids can be increased and the seedling rate can be improved by "externally spraying 6-BA onto the flower bud", "adding phytic acid into the medium during microspore culture" and "adjusting the spectral and temperature conditions during embryoid regeneration.

Compared with the prior art, the present invention has the advantages that:

(1) in the present invention, creatively by externally spraying 6-BA onto the flower bud to obtain high-activity microspores, by adding phytic acid into the medium in the process of microspore culture to improve the oxidation resistance ability of the microspores, and then by adjusting the red-blue ratio of the spectrum in the process of microspore regeneration to regulate the hormone level, photoautotrophy ability and morphogenesis of the microspores, while reducing the temperature of the culture environment simultaneously, the cultured embryos can be more easily developed into normal plants directly, thereby improving the one-time seedling rate of the microspore embryos of *Brassica campestris ssp. Chinensis Makino*; and the present invention solves a series of production and application problems of *Brassica campestris ssp. Chinensis Makino* in long cross breeding period, low breeding efficiency, and difficulty in obtaining and preserving the mutant germplasm resources in the process of breeding; and (2) The method provided by the present invention has the advantages of simple operation, a short production cycle, high efficiency, etc., and the method as used avoids the use of high-risk, highly toxic or explosive reagents, and has obvious safety.

DESCRIPTION OF THE EMBODIMENTS

The embodiments of the present invention will be described in detail hereafter. The embodiments are implemented on the premise of the technical solution of the present invention, and detailed implementation and a specific operation process are given. However, the claimed scope of the present invention is not limited to the following examples.

Example 1

In this example, a method for improving a one-time seedling rate of microspore embryoids of *Brassica campestris ssp. Chinensis Makino* included the steps of:

(1) pretreatment of flower bud a concentration of 50 mg/L of 6-BA was sprayed onto a flower bud of a plant of *Brassica campestris ssp. Chinensis Makino* at a full-bloom stage after squaring; on the second day after the spraying of 6-BA, an inflorescence, which was specifically a main inflorescence or a healthy inflorescence of a primary branch of a plant without insect pests and cracked buds, was selected, placed in a self-sealing bag and sprayed with clean water, and then stored in a refrigerator at 4° C. for 1 day for later use;

(2) isolation of microspores a flower bud with a petal length/anther length between 0.5-1 was selected, firstly sterilized with 70% alcohol for 30 s, then sterilized with 0.1% $HgCl_2$ under shaking for 6 min, and then rinsed with sterilized water for 2 times, with each time for 5 min; then, the flower bud was crushed in a B5 medium with a glass rod to release microspores, and the microspores were filtered by a 300-mesh steel-wire mesh screen and a cell mesh screen successively; subsequently, a filtrate was collected into a centrifugal tube and centrifuged under the condition of 1,000 r/min for 3 min; and after the centrifuging, a pellet was resuspended with a B5 medium, and the resuspended solution was centrifuged again under the condition of 1,000 r/min for 3 min to obtain a pellet as the purified microspores desired for the objective;

(3) culture of microspores the purified microspores were diluted with a NLN medium, and a cell density was adjusted to about $1 \times 10^5$ /mL$^{-1}$ (at this time, the medium was pale yellow); subsequently, the diluted purified microspores were subpackaged into culture dishes, and added with phytic acid PA at a concentration of 0.01%; and finally, the microspores were subjected to heat shock treatment at 33° C. for 24 h, then transferred to culture in the dark at 25° C., and placed onto a shaker for shaking culture after embryoids visible to naked eyes appeared; and (4) germination and seedling of embryoids the cultured embryoids in a cotyledon stage with a length of 2.5 mm were transferred onto a MS medium for differentiation culture, wherein culture conditions were 4° C., 14 h of illumination by blue-red compound light/day, and 14 days of culture; and then, the culture was continued under a condition of 25° C. and 14 h of illumination by blue-red compound light/day until seedling; wherein the ratio of blue light to red light in the blue-red compound light was 1:1.

Example 2

In this example, a method for improving a one-time seedling rate of microspore embryoids of *Brassica campestris ssp. Chinensis Makino* included the steps of:

(1) pretreatment of flower bud a concentration of 100 mg/L of 6-BA was sprayed onto a flower bud of a plant of *Brassica campestris ssp. Chinensis Makino* at a full-bloom stage after squaring; on the second day after the spraying of 6-BA, an inflorescence, which was specifically a main inflorescence or a healthy inflorescence of a primary branch of a plant without insect pests and cracked buds, was selected, placed in a self-sealing bag and sprayed with clean water, and then stored in a refrigerator at 4° C. for 2 day for later use;

(2) isolation of microspores a flower bud with a petal length/anther length between 0.5-1 was selected, firstly sterilized with 70% alcohol for 30 s, then sterilized with 0.1% HgCl$_2$ under shaking for 6 min, and then rinsed with sterilized water for 3 times, with each time for 5 min; then, the flower bud was crushed in a B5 medium with a glass rod to release microspores, and the microspores were filtered by a 300-mesh steel-wire mesh screen and a cell mesh screen successively; subsequently, a filtrate was collected into a centrifugal tube and centrifuged under the condition of 1,000 r/min for 3 min; and after the centrifuging, a pellet was resuspended with a B5 medium, and the resuspended solution was centrifuged again under the condition of 1,000 r/min for 3 min to obtain a pellet as the purified microspores desired for the objective;

(3) culture of microspores the purified microspores were diluted with a NLN medium, and a cell density was adjusted to about $1.5 \times 10^5$ /mL$^{-1}$ (at this time, the medium was pale yellow); subsequently, the diluted purified microspores were subpackaged into culture dishes, and added with phytic acid PA at a concentration of 0.1%; and finally, the microspores were subjected to heat shock treatment at 33° C. for 24 h, then transferred to culture in the dark at 25° C., and placed onto a shaker for shaking culture after embryoids visible to naked eyes appeared; and (4) germination and seedling of embryoids the cultured embryoids in a cotyledon stage with a length of 2.6 mm were transferred onto a MS medium for differentiation culture, wherein culture conditions were 4° C., 14 h of illumination by blue-red compound light/day, and 14 days of culture; and then, the culture was continued under a condition of 25° C. and 14 h of illumination by blue-red compound light/day until seedling; wherein the ratio of blue light to red light in the blue-red compound light was 1:1.

Example 3

In this example, a method for improving a one-time seedling rate of microspore embryoids of *Brassica campestris ssp. Chinensis Makino* included the steps of:

(1) pretreatment of flower bud a concentration of 100 mg/L of 6-BA was sprayed onto a flower bud of a plant of *Brassica campestris ssp. Chinensis Makino* at a full-bloom stage after squaring; on the second day after the spraying of 6-BA, an inflorescence, which was specifically a main inflorescence or a healthy inflorescence of a primary branch of a plant without insect pests and cracked buds, was selected, placed in a self-sealing bag and sprayed with clean water, and then stored in a refrigerator at 4° C. for 1 day for later use;

(2) isolation of microspores a flower bud with a petal length/anther length between 0.5-1 was selected, firstly sterilized with 70% alcohol for 30 s, then sterilized with 0.1% HgCl$_2$ under shaking for 6 min, and then rinsed with sterilized water for 2 times, with each time for 5 min; then, the flower bud was crushed in a B5 medium with a glass rod to release microspores, and the microspores were filtered by a 300-mesh steel-wire mesh screen and a cell mesh screen successively; subsequently, a filtrate was collected into a centrifugal tube and centrifuged under the condition of 1,000 r/min for 3 min; and after the centrifuging, a pellet was resuspended with a B5 medium, and the resuspended solution was centrifuged again under the condition of 1,000 r/min for 3 min to obtain a pellet as the purified microspores desired for the objective;

(3) culture of microspores the purified microspores were diluted with a NLN medium, and a cell density was adjusted to about $1.5 \times 10^5$ /mL$^{-1}$ (at this time, the medium was pale yellow); subsequently, the diluted purified microspores were subpackaged into culture dishes, and added with phytic acid PA at a concentration of 0.15%; and finally, the microspores were subjected to heat shock treatment at 33° C. for 24 h, then transferred to culture in the dark at 25° C., and placed onto a shaker for shaking culture after embryoids visible to naked eyes appeared; and (4) germination and seedling of embryoids the cultured embryoids in a cotyledon stage with a length of 2.8 mm were transferred onto a MS medium for differentiation culture, wherein culture conditions were 4° C., 14 h of illumination by blue-red compound light/day, and 14 days of culture; and then, the culture was continued under a condition of 25° C. and 14 h of illumination by blue-red compound light/day until seedling; wherein the ratio of blue light to red light in the blue-red compound light was 1:1.

Example 4

In this example, a method for improving a one-time seedling rate of microspore embryoids of Brassica campestris ssp. Chinensis Makino included the steps of:

(1) pretreatment of flower bud
   a concentration of 150 mg/L of 6-BA was sprayed onto a flower bud of a plant of Brassica campestris ssp. Chinensis Makino at a full-bloom stage after squaring; on the second day after the spraying of 6-BA, an inflorescence, which was specifically a main inflorescence or a healthy inflorescence of a primary branch of a plant without insect pests and cracked buds, was selected, placed in a self-sealing bag and sprayed with clean water, and then stored in a refrigerator at 4° C. for 2 day for later use;

(2) isolation of microspores
   a flower bud with a petal length/anther length between 0.5-1 was selected, firstly sterilized with 70% alcohol for 30 s, then sterilized with 0.1% $HgCl_2$ under shaking for 6 min, and then rinsed with sterilized water for 3 times, with each time for 5 min; then, the flower bud was crushed in a B5 medium with a glass rod to release microspores, and the microspores were filtered by a 300-mesh steel-wire mesh screen and a cell mesh screen successively; subsequently, a filtrate was collected into a centrifugal tube and centrifuged under the condition of 1,000 r/min for 3 min; and after the centrifuging, a pellet was resuspended with a B5 medium, and the resuspended solution was centrifuged again under the condition of 1,000 r/min for 3 min to obtain a pellet as the purified microspores desired for the objective;

(3) culture of microspores
   the purified microspores were diluted with a NLN medium, and a cell density was adjusted to about $2 \times 10^5$ /$mL^{-1}$ (at this time, the medium was pale yellow); subsequently, the diluted purified microspores were subpackaged into culture dishes, and added with phytic acid PA at a concentration of 0.5%; and finally, the microspores were subjected to heat shock treatment at 33° C. for 24 h, then transferred to culture in the dark at 25° C., and placed onto a shaker for shaking culture after embryoids visible to naked eyes appeared; and (4) germination and seedling of embryoids
   the cultured embryoids in a cotyledon stage with a length of 3 mm were transferred onto a MS medium for differentiation culture, wherein culture conditions were 4° C., 14 h of illumination by blue-red compound light/day, and 14 days of culture; and then, the culture was continued under a condition of 25° C. and 14 h of illumination by blue-red compound light/day until seedling; wherein the ratio of blue light to red light in the blue-red compound light was 1:1.

Example 5

This example was used for verifying the effects of different concentrations of 6-BA on the embryogenesis rate of Brassica campestris ssp. Chinensis Makino:

Method: in the pretreatment process of the flower buds, after squaring of Brassica campestris ssp. Chinensis Makino, at the full flowering stage, 6-BA solutions with concentrations of 0, 50, 100, 150 and 200 mg/L were prepared and sprayed onto the flower buds respectively, so as to study the effects of different concentrations of 6-BA on the embryogenesis rate of Brassica campestris ssp. Chinensis Makino (other steps were the same, and were conducted with reference to Example 3).

Implementation result: the result was shown in Table 1.

TABLE 1

Effects of different concentrations of 6-BA on the embryogenesis rate of Brassica campestris ssp. Chinensis Makino

| Concentration of 6-BA (mg/L) | Average embryogenesis rate (embryo/bud) |
| --- | --- |
| 0 | 0.78 |
| 50 | 0.92 |
| 100 | 1.56 |
| 150 | 1.08 |
| 200 | 0.74 |

It could be seen from Table 1 that compared with the normally growing Brassica campestris ssp. Chinensis Makino, the embryogenesis rates of the flower buds treated with 6-BA solutions had different degrees of change. Among them, the best effect is achieved in the flower bud sprayed with 100 mg/L of the 6-BA solution, with the embryogenesis rate being increased by 100%; the second is the flower bud sprayed with 150 mg/L and 50 mg/L of the 6-BA solution, with the embryogenesis rate being increased by 17.95% and 38.46% respectively; and the embryogenesis rate of the flower bud sprayed with 200 mg/L of the 6-BA solution was inhibited, which was decreased by 5.13% compared with that without application of the 6-BA solution.

Example 6

This example was used for verifying the effects of different concentrations of phytic acid PA on the embryogenesis rate of Brassica campestris ssp. Chinensis Makino:

Method: in the process of microspore culture, the purified microspores subjected to density dilution were subpackaged into culture dishes, and added with phytic acid PA at concentrations of 0, 0.01%, 0.1%, 0.15%, 0.5% and 1% respectively, so as to study the effects of different concentrations of phytic acid PA on the embryogenesis rate of Brassica campestris ssp. Chinensis Makino (other steps were the same, and conducted with reference to Example 3).

Implementation result: the result was shown in Table 2.

TABLE 2

Effects of different concentrations of phytic acid on the embryogenesis rate of Brassica campestris ssp. Chinensis Makino

| Concentration of PA (%) | Average embryogenesis rate (embryo/bud) |
| --- | --- |
| 0 | 0.639 |
| 0.01 | 0.774 |
| 0.1 | 1.495 |
| 0.15 | 1.137 |
| 0.5 | 0.789 |
| 1 | 0.487 |

It could be seen from Table 2 that, compared with the medium without addition of PA, the embryogenesis rates were increased by 21%, 134%, 78% and 23% when 0.01%, 0.1%, 0.15% and 0.5% of PA were added into the medium respectively, while the embryogenesis rate was inhibited and decreased by 24% when a concentration of 1% of PA was added.

Example 7

This example was used for verifying the effects of different spectral and low-temperature treatment on embryoid regeneration:

Method: in the process of germination and seedling of the embryoids, the cultured embryoids in a cotyledon stage were transferred onto a MS medium, and placed under four different light qualities for differentiation culture for 14 days (14 h of illumination/day), and two temperature groups were set for each light quality: a 4° C. treatment group and a 25° C. control group; and then culture was conducted at 25° C. under the 14 h illumination condition (with the same light qualities as above) until seedling. After 4 weeks, the direct seedlings of the microspores of *Brassica campestris ssp. Chinensis Makino* were counted, so as to further study the effects of different spectral and low-temperature treatment on the embryoid regeneration (other steps were the same, and conducted with reference to Example 3).

Different light qualities refer to the corresponding light qualities under treatment with red light, blue light, the blue-red compound light (1:1) and a fluorescent lamp respectively, and their main technical parameters were shown in Table 3.

Implementation result: the result was shown in Table 4.

TABLE 3

Main technical parameters of different spectral distributions

| Light quality | Peak value $\lambda_p$ (nm) | Half wave width $\Delta \lambda$ (nm) | Illumination intensity ($\mu$ mol/m2·s) |
|---|---|---|---|
| Red light | 660 | 5 ~ 10 | 100 |
| Blue light | 660/460 | 5 ~ 10 | 100 |
| Blue-red compound light (1:1) | 660/460 | 5 ~ 10 | 100 |
| Fluorescent lamp | 380 ~ 760 | - | 100 |

TABLE 4

Effects of different spectral and low-temperature treatment on embryoid regeneration

| Optical treatment | Temperature (°C) | Embryo number | Number of seedlings | Regeneration rate (%) | Significant |
|---|---|---|---|---|---|
| Red light | 4 | 100 | 28.15 | 0.2815 | f |
|  | 25 | 100 | 21.05 | 0.2105 | g |
| Blue light | 4 | 100 | 39.48 | 0.3948 | c |
|  | 25 | 100 | 32.85 | 0.3285 | e |
| Blue-red compound light (1:1) | 4 | 100 | 48.55 | 0.4855 | a |
|  | 25 | 100 | 39.85 | 0.3985 | c |
| Fluorescent lamp | 4 | 100 | 44.05 | 0.4405 | b |
|  | 25 | 100 | 38.35 | 0.3835 | d |

It could be seen from Table 4 that, the well-grown cotyledon embryoids would have different degrees of change in the direct seedling rate when they are transferred into MS media and placed under four different light qualities for differentiation culture. Among them, the best effect is achieved by treatment with blue-red compound light, with the direct seedling rate being increased by 3.91% compared with that of the control white fluorescent lamp; and the direct seedling rates were inhibited to different degrees by individual blue light and red light, which were decreased by 14.34% and 45.11% compared with the control, respectively.

Meanwhile, during seedling by embryoid regeneration, low-temperature pretreatment would also affect the direct seedling rate. When the microspores treated with the red light were placed at a low temperature of 4° C. for 14 days, the direct seedling rate was increased by 33.73% compared with that at 25° C.; the direct seedling rate was increased by 20.18% after the microspores treated with the blue light were subjected to a low temperature; the direct seedling rate was increased by 21.83% after the microspores treated with the blue-red compound light were subjected to a low temperature; and the direct seedling rate was increased by 14.86% after the microspores treated with the white fluorescent lamp were subjected to a low temperature; so that the low-temperature treatment could improve the one-time seedling rate of the embryoids.

In conclusion, among all the combinations, the combination of illumination with the blue-red compound light and low-temperature treatment at 4° C. had the best effect on the one-time seedling rate of the embryoids, which was increased by 26.60% compared with that of the combination of illumination with the fluorescent lamp and placement at room temperature of 25° C.

The aforementioned description is only preferred embodiments of the present invention, rather than limiting the present invention, and any modification, equivalent substitution, improvement and the like made within the spirit and principle of the present invention should be included in the claimed scope of the present invention.

What is claimed is:

1. A method for improving a one-time seedling rate of microspore embryoids of Brassica campestris ssp. Chinensis Makino, comprising the steps of:
   (1) pretreatment of flower bud
   spraying a concentration of 50-150 mg/L of 6-Benzylaminopurine (6-BA) onto a flower bud of a plant of Brassica campestris ssp. Chinensis Makino after squaring; and taking an inflorescence for later use on the next day after the spraying of the 6-BA;
   (2) isolation of microspores
   selecting a flower bud with a petal length/anther length between 0.5-1, conducting combined sterilization with 70% alcohol and 0.1% HgCl2, and then rinsing with sterilized water; then, crushing the bud in a B5 medium to release microspores, and filtering the microspores by a steel-wire mesh screen and a cell mesh screen successively; subsequently, collecting a filtrate into a centrifugal tube for centrifuging; and after the centrifuging, resuspending a pellet with B5 medium and centrifuging again to obtain a pellet as desired purified microspores;
   (3) culture of microspores
   diluting the purified microspores with NLN medium, and adjusting a cell density to $1 \times 10^5 - 2 \times 10^5$/mL-1; subsequently, subpackaging the diluted purified microspores into culture dishes, and adding phytic acid (PA) at a concentration of 0.01%-0.5%; and finally, subjecting to heat shock treatment at 33°C for 24 h, then transferring to culture in the dark at 25°C, and placing onto a shaker for shaking culture after embryoids visible to naked eyes appear; and
   (4) germination and seedling of embryoids
   transferring the cultured embryoids in a cotyledon stage onto MS medium for differentiation culture, wherein culture conditions are: 4°C, 14 h of illumination by blue-red compound light/day, and 14 days of culture; and then, continuing to culture under a condition of 25°C and 14 h of illumination by blue-red compound light/day until seedling.

2. The method for improving a one-time seedling rate of microspore embryoids of Brassica campestris ssp. Chinensis Makino according to claim 1, wherein in the step (1), the selected inflorescence is specifically a main inflorescence or a healthy inflorescence of a primary branch of a plant without insect pests and cracked buds.

3. The method for improving a one-time seedling rate of microspore embryoids of Brassica campestris ssp. Chinensis Makino according to claim 1, wherein in the step (1), after selected, the corresponding inflorescence is placed in a self-sealing bag and sprayed with clean water, and then stored in a refrigerator at 4°C for 1-2 days for later use.

4. The method for improving a one-time seedling rate of microspore embryoids of Brassica campestris ssp. Chinensis Makino according to claim 1, wherein in the step (2), a specific method of combined sterilization of the flower bud is: firstly sterilizing with 70% alcohol for 30 s, and then sterilizing with 0.1% HgCl2 under shaking for 6 min; and after the combined sterilization is completed, the flower bud is rinsed with sterilized water for 2-3 times, with each time for 5 min.

5. The method for improving a one-time seedling rate of microspore embryoids of Brassica campestris ssp. Chinensis Makino according to claim 1, wherein in the step (2), after the sterilization and cleaning of the selected bud is completed, the bud is crushed in the B5 medium with a glass rod to release the microspores, and then filtered by a 300 mesh steel-wire mesh screen and a cell mesh screen successively; subsequently, the filtrate is collected in a centrifuge tube and centrifuged under a condition of 1,000 r/min for 3 min; and after the centrifugation, the pellet is resuspended with the B5 medium and the resuspended solution is centrifuged again at 1,000 r/min for 3 min, and the finally obtained pellet is the purified microspores desired for the objective.

6. The method for improving a one-time seedling rate of microspore embryoids of Brassica campestris ssp. Chinensis Makino according to claim 1, wherein in the step (3), the culture medium is pale yellow when the cell density of the microspores is $1 \times 10^5 - 2 \times 10^5/mL^{-1}$.

7. The method for improving a one-time seedling rate of microspore embryoids of Brassica campestris ssp. Chinensis Makino according to claim 1, wherein in the step (4), a length of the embryoids in a cotyledon stage transferred onto the MS medium is 2.5-3 mm.

* * * * *